(12) United States Patent
Fathallah et al.

(10) Patent No.: US 8,926,562 B2
(45) Date of Patent: Jan. 6, 2015

(54) SYRINGE HOLDING SYSTEM

(75) Inventors: Marwan A. Fathallah, Mundelein, IL (US); Scott I. Biba, Highland, WI (US); William E. Tourdot, Saint Paul, MN (US)

(73) Assignee: Hospira, Inc., Lake Forest, IL (US)

(*) Notice: Subject to any disclaimer, the term of this patent is extended or adjusted under 35 U.S.C. 154(b) by 1783 days.

(21) Appl. No.: 11/322,675

(22) Filed: Dec. 30, 2005

(65) Prior Publication Data

US 2007/0156091 A1     Jul. 5, 2007

(51) Int. Cl.
*A61M 1/00* (2006.01)
*F16L 3/08* (2006.01)
*F16L 3/12* (2006.01)
*A61M 5/14* (2006.01)
*A61M 39/02* (2006.01)

(52) U.S. Cl.
CPC ............ *A61M 5/1418* (2013.01); *A61M 39/02* (2013.01); *A61M 2205/12* (2013.01)
USPC .......................... 604/151; 248/74.1; 248/74.2

(58) Field of Classification Search
USPC .......... 604/20, 66, 240, 19, 151; 248/229.11, 248/229.15, 316.2, 328, 231.71, 226.11, 248/308, 213.2, 207, 74.1, 74.2
See application file for complete search history.

(56) References Cited

U.S. PATENT DOCUMENTS

| | | | |
|---|---|---|---|
| 1,647,039 A | | 4/1927 | Fischer |
| 4,211,380 A | * | 7/1980 | Lillegard et al. ......... 248/229.15 |
| 4,644,960 A | * | 2/1987 | Johans .......................... 607/122 |
| 4,840,345 A | * | 6/1989 | Neil et al. ..................... 248/74.2 |
| 4,935,014 A | | 6/1990 | Haber |
| 5,102,083 A | | 4/1992 | Baskas |
| 5,609,572 A | | 3/1997 | Lang |
| 5,681,019 A | * | 10/1997 | Boyce ....................... 248/229.11 |
| 5,709,663 A | | 1/1998 | Younkes |
| 5,772,166 A | * | 6/1998 | Adams ...................... 248/231.81 |
| 5,807,345 A | | 9/1998 | Grabenkort |
| D424,692 S | | 5/2000 | Monaghan et al. |
| 6,565,054 B2 | | 5/2003 | Weesner et al. |
| 6,726,657 B1 | | 4/2004 | Dedig et al. |
| 7,140,070 B2 | * | 11/2006 | Yuta et al. ........................... 16/4 |
| 7,850,659 B1 | * | 12/2010 | Trombley et al. ............. 604/174 |
| 2005/0177110 A1 | | 8/2005 | Azzolini |

* cited by examiner

*Primary Examiner* — Matthew F Desanto
(74) *Attorney, Agent, or Firm* — Michael R. Crabb

(57) ABSTRACT

A syringe holder includes a body with a syringe retainer, an elongated finger and a stop member connected to the body. The finger inserts longitudinally into a socket on a pump without the aid of tools and permits the holder to move in multiple planes. The stop member limits such movement. The stop member can include a clip for releasably clamping onto a portion of a pump. The syringe retainer can include a hole in the body and may optionally include an adaptor mounted in or extending into the hole for detachably attaching a syringe. The syringe holder can be incorporated into a tube set assembly or an infusion system.

29 Claims, 5 Drawing Sheets

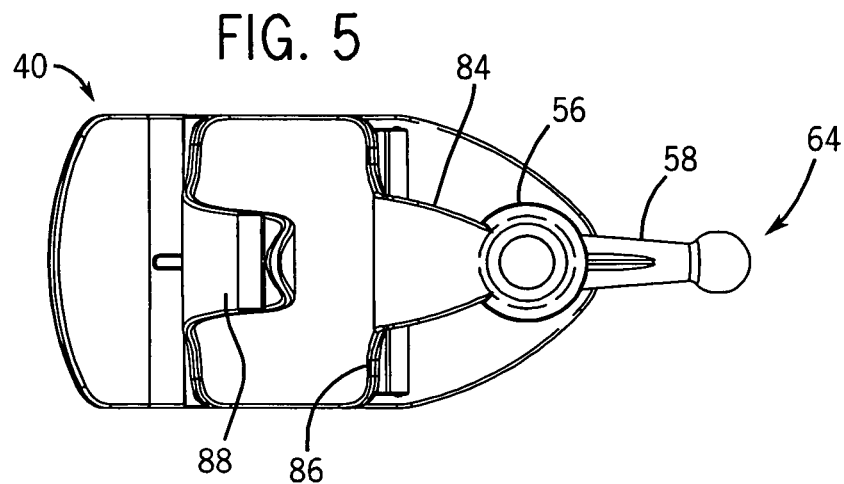
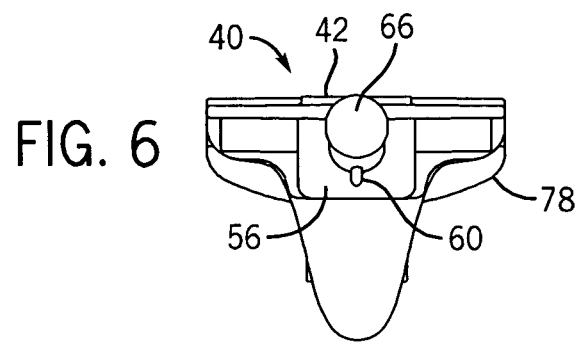
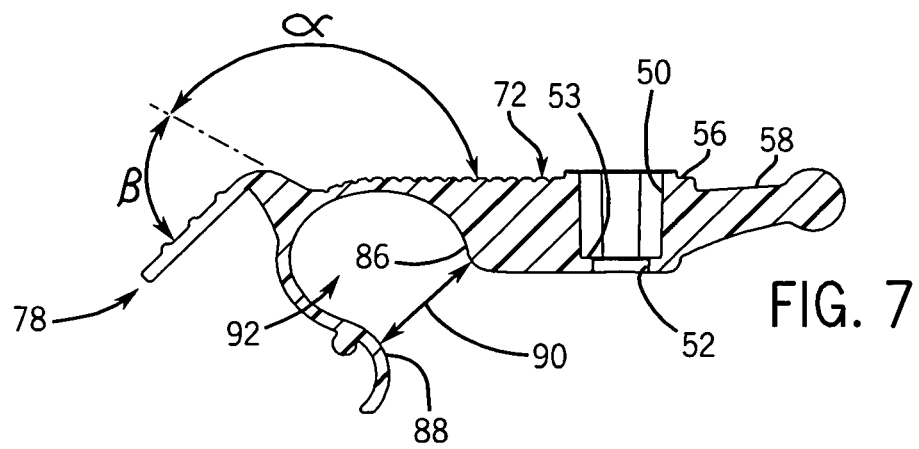

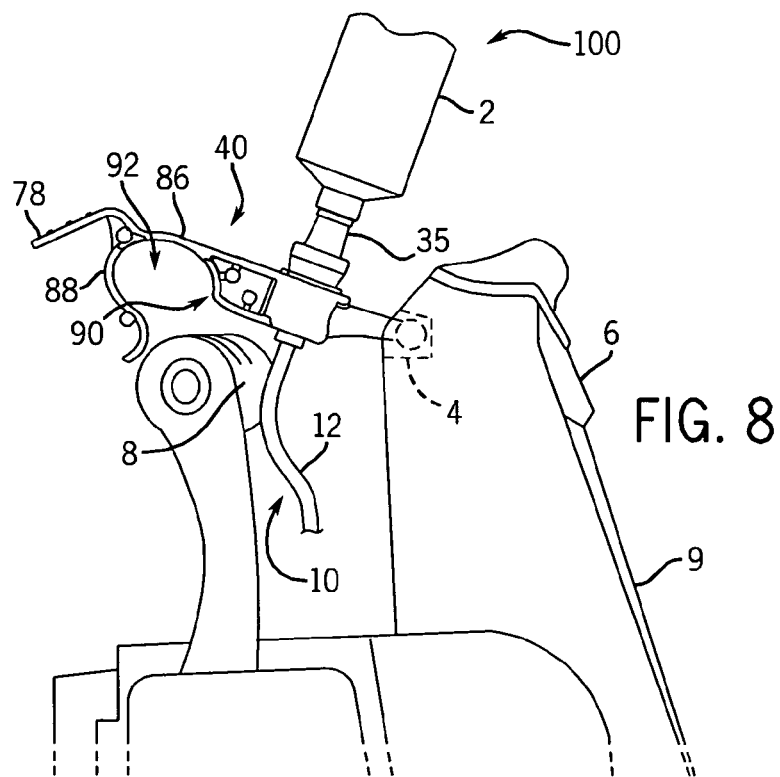

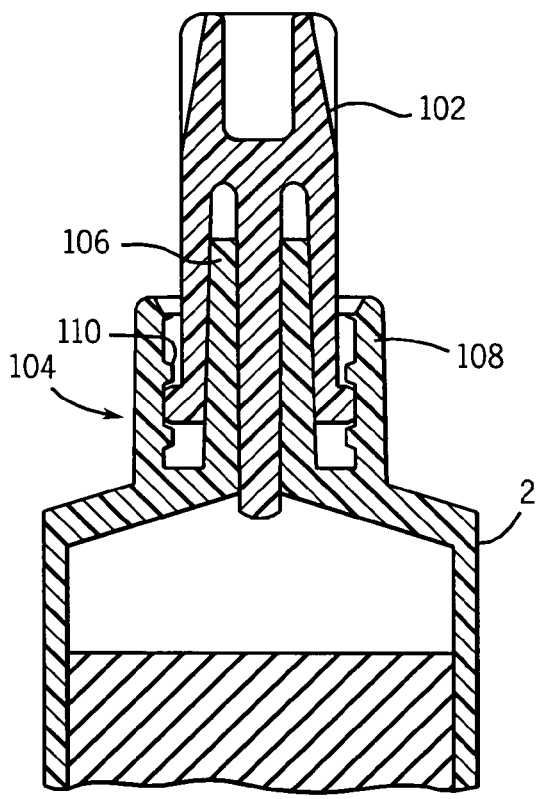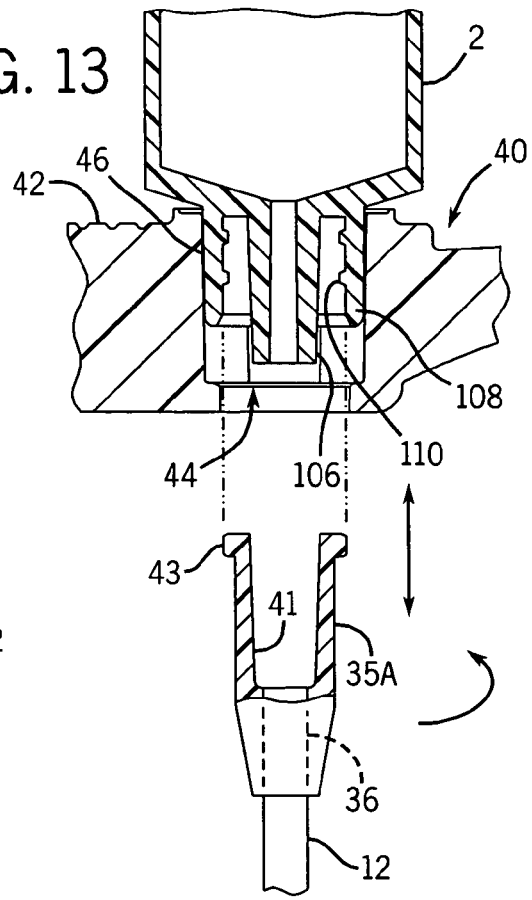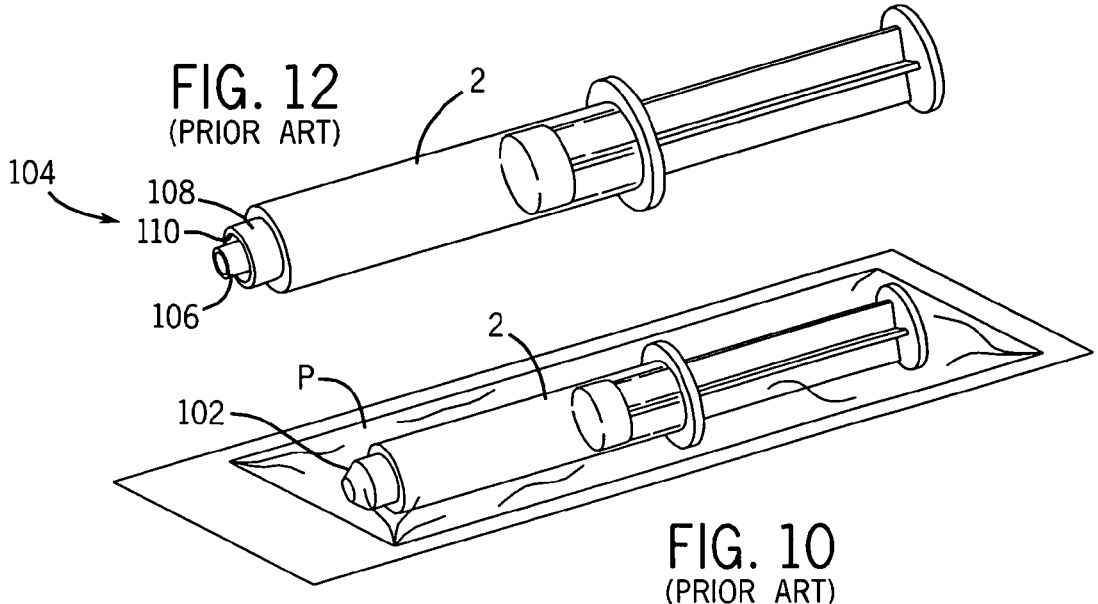

SYRINGE HOLDING SYSTEM

BACKGROUND OF THE INVENTION

The present invention generally relates to the field of medical devices. More particularly, the invention relates to a syringe holding system for detachably mounting a syringe on a medical pump. The syringe holding system includes a syringe holder, which can be incorporated into a medical tube set assembly or an infusion system.

The syringe is a medical device that is often used to deliver fluids such as drugs, contrast agents, and the like. In fact, many drugs are prepackaged in syringes for delivery. However, there is a need to hold the syringe in the proper orientation while applying force to the plunger or piston of the syringe to expel fluid.

Some motorized infusion pumps utilize a syringe mounted thereon and a motor driven plunger driver assembly for moving the syringe plunger to expel fluid. The mounting mechanisms are often complex and costly to produce.

Other motorized infusion pumps utilize peristaltic action on a tube or reciprocating action of a driver on the elastic diaphragm of a cassette to deliver fluid. However, even with these pumps there is sometimes a need or desire to use a syringe to give a concentrated bolus, supplement or interrupt an infusion of a primary drug to provide a second drug. Sometimes a second pole stand can be used to hang the syringe or secondary bag, but this requires additional space at the patient's bedside. Such additional bedside space may not be readily available. A caregiver can manually hold the syringe, but this can be tedious, detracts from two-handed caregiver tasks, and is inefficient.

Thus, there is a need for a syringe holding system that is efficient, practical to use, and cost-effective to manufacture.

A further object of the present invention is the provision of a tube set assembly including a syringe holder for detachably mounting a syringe to a medical pump.

These and other objects will be apparent to those skilled in the art.

SUMMARY OF THE INVENTION

The present invention generally relates to a syringe holding system for detachably mounting a syringe on a medical pump. The syringe holding system includes a syringe holder, which can be incorporated into a medical tube set assembly or an infusion system.

The syringe holder of this invention includes a body. A syringe retainer is connected to the body. An elongated finger connects to and extends outwardly from the body. The finger is adapted to be inserted longitudinally without aid of tools into a socket on a medical pump so as to permit pivotal movement of the syringe holder in a plurality of planes once inserted. A stop member connected to the body limits the pivotal movement of the syringe holder.

In one aspect of the invention the stop member is a clip that has jaws that releasably clamp onto a portion of the pump, such as the pump handle for example, to limit the pivotal movement of the syringe holder and thereby removably or detachably mount the syringe holder in a desired fixed position on the pump. The body, finger and clip of the syringe holder advantageously can be formed of a single unitary piece of material, which can be cost-effectively produced using plastics and conventional molding techniques.

In another aspect of the invention the syringe retainer includes a mounting hole in the body, preferably located between the finger and the stop member. The syringe is directly inserted into the hole and is thus directly retained in a desired orientation. Alternatively, the syringe retainer can include an adaptor detachably attachable to the syringe. The adaptor can be loosely received or rigidly mounted in the mounting hole on the body. The adaptor can be fluidly connected to the tube of a tube set assembly. The mounting hole indirectly retains the syringe in the desired orientation in conjunction with the adaptor.

Other features, aspects and advantages of the syringe holding system will become readily apparent from the following detailed description, the accompanying drawings, and the appended claims.

BRIEF DESCRIPTION OF THE DRAWINGS

FIG. 5 is bottom view of the syringe holder of FIG. 2.

FIG. 6 is a front elevation view of the syringe holder of FIG. 2.

FIG. 7 is a sectional view of the syringe holder of the present invention taken along line 7-7 in FIG. 4.

FIG. 8 is partial side elevation view of a pump with the syringe holder of the present invention being used to mount a tube set assembly including a syringe to the pump.

FIG. 9 is a partial perspective view of the pump from FIG. 8 with the syringe holder and syringe in the installed position.

FIG. 10 is a perspective view of a conventional pre-filled, capped and packaged syringe.

FIG. 11 is a partial central longitudinal cross-sectional view of the pre-filled syringe and cap from FIG. 10.

FIG. 12 is a perspective view of the syringe of FIG. 10 with the packaging and cap removed.

FIG. 13 is a partial sectional view similar to FIG. 7 and shows another embodiment of the syringe holder of the present invention wherein the syringe is mounted directly in the mounting hole.

DETAILED DESCRIPTION OF THE PREFERRED EMBODIMENTS

Figure 1:
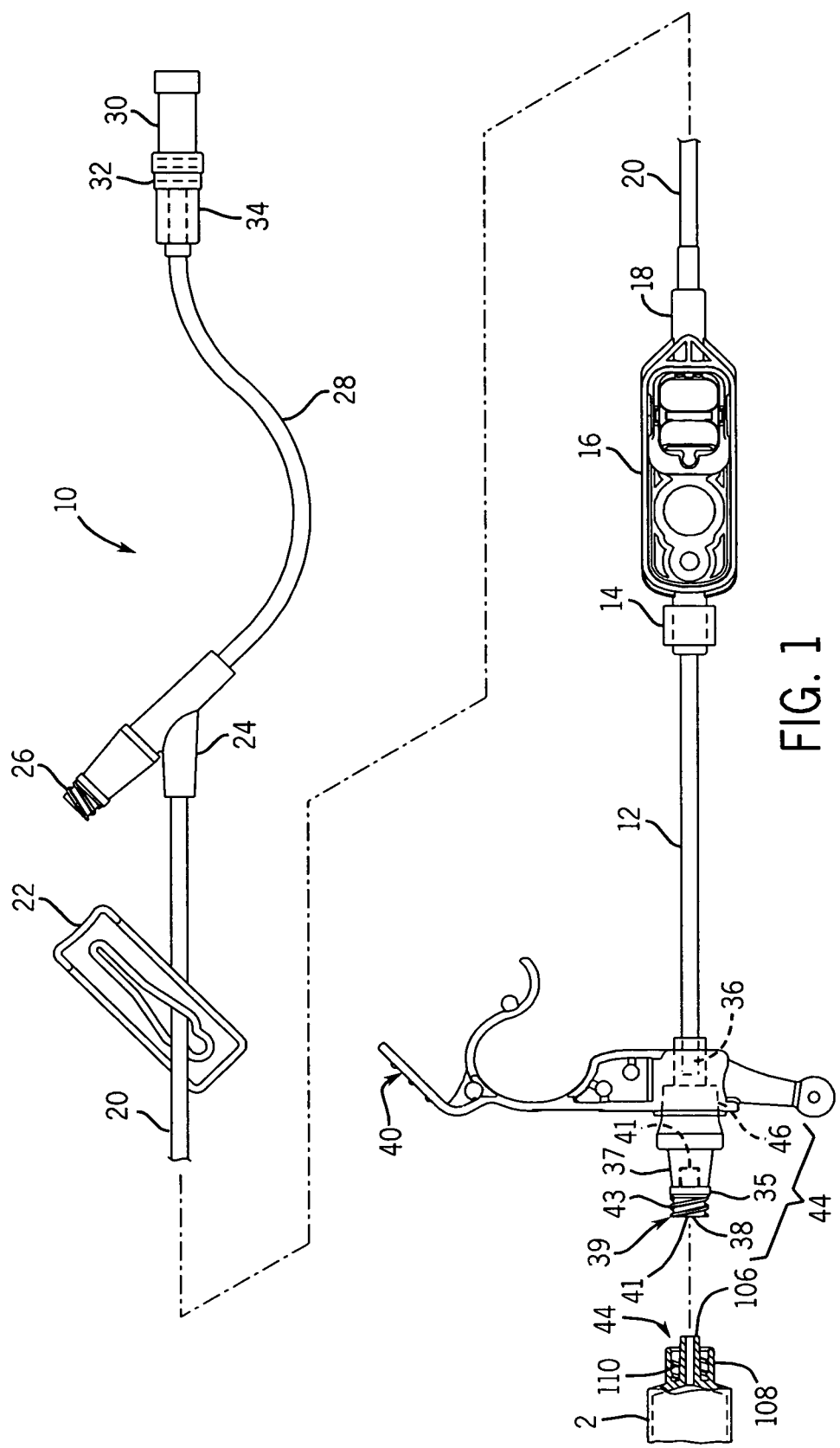
FIG. 1 is a perspective view of a tube set assembly that includes a syringe holder according to the present invention.
Figure 2:
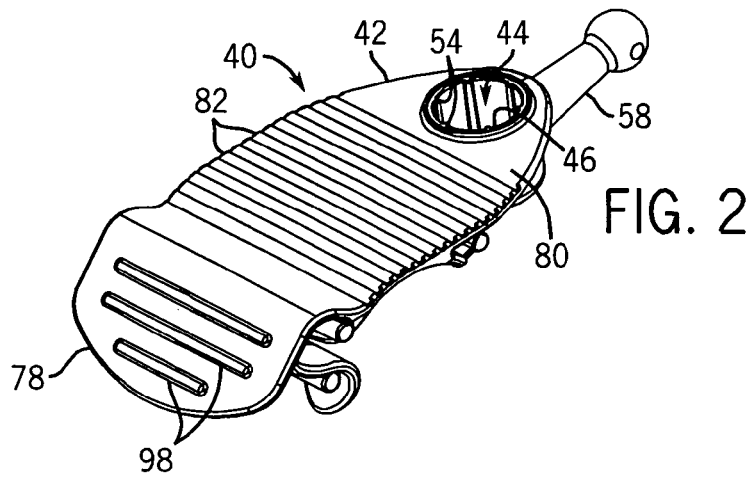
FIG. 2 is a perspective view of a syringe holder according to one embodiment of the present invention.
Figure 3:
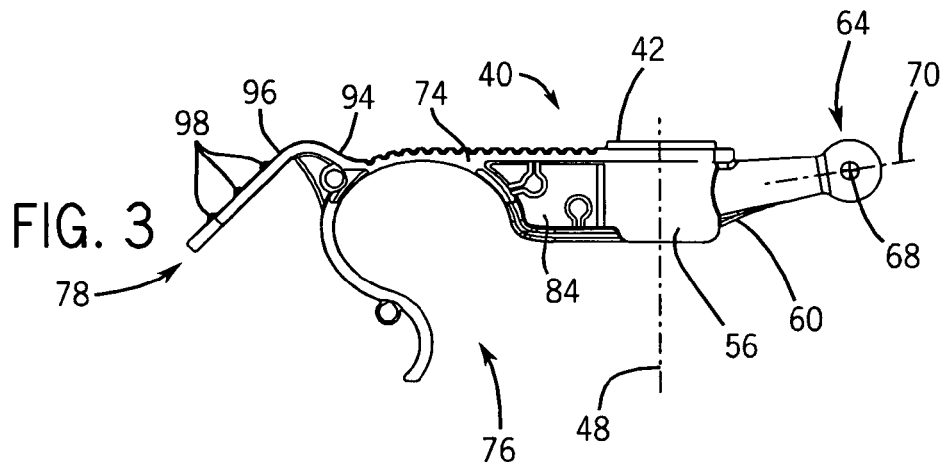
FIG. 3 is a side elevation view of the syringe holder of FIG. 2.

While the present invention is susceptible of embodiment in various forms, there is shown in the drawings and will be described hereinafter a presently preferred embodiment, with the understanding that the present disclosure is to be considered as an exemplification of the invention, and is not intended to limit the invention to the specific embodiment or embodiments illustrated.

FIG. 1 shows a tube set assembly 10 including a syringe holder 40 according to the present invention. The tube set assembly 10 includes a first tube 12 with a distal end fluidly connected with the inlet 14 of a pump cassette 16. The pump cassette 16 has an outlet 18 to which a second tube 20 is fluidly connected. The tube set assembly 10 can include other components downstream from the pump cassette 16. Because such components are either optional or not particularly relevant to the invention disclosed herein, they are only described briefly below. A slide clamp 22 is operatively attached to the second tube 20. A Y-site 24, which has an integral one-way valve 26, fluidly connects to the second tube 20 and the proximal end of a third tube 28. A male distal adaptor 30 fluidly connects to the distal end of the third tube 28 and provides the capability to connect to an IV needle or catheter (not shown) to deliver fluid to a patient. The male adaptor 30 includes an air filter 32 and a locking collar 34 for securing the tube set assembly 10 to the IV needle or catheter.

The proximal end of the first tube 12 fluidly connects to an adaptor 35 such as a LIFESHIELD® CLAVE® connector commercially available from Hospira, Inc. of Lake Forest, Ill., USA, for example. This connection can be made by a variety of known connection means, including but not limited to inserting the proximal end of the tube 12 into a mating hole 36 formed in the body 37 of the adaptor 35 and applying a conventional solvent sealer or by providing mating female and male luer lock connectors on the adaptor 35 and tube 12. The adaptor 35 includes a one-way valve 39 thereon. The end of the body 37 opposite from the tube 12 including securing means 39, including but not limited to a female luer cup 41 and external locking threads 43, in order to fluidly connect a conventional needleless syringe 2, such as shown in FIGS. 10-12 for example, to the adaptor 35.

Referring to FIGS. 2-7, the syringe holder 40 has a body 42 and provides a syringe retainer or means 44 for retaining the syringe 2. In one embodiment of the invention, the syringe retainer 44 includes a mounting hole 46, which may receive the syringe 2 directly (FIG. 13) or indirectly through the adaptor 35 (FIG. 1) described above. The mounting hole 46 defines a syringe orientation axis 48 that is substantially upright. The mounting hole 46 has an upper portion 50 and a lower portion 52. The upper portion 50 has a diameter that is larger than the diameter of the lower portion 52. Thus, a shoulder or annular ledge 53 is formed between the upper portion 50 and the lower portion 52 of the mounting hole 46.

The syringe retaining means 44 can optionally further include at least one groove or rib 54 formed on the peripheral surface of the upper portion 50. In the case of a rib, the rib extends inwardly toward the syringe orientation axis 48. In the case of a groove, the groove extends away from the syringe orientation axis 48. In both cases, the groove or rib 54 extends downwardly toward the lower portion 52. In one embodiment, the groove or rib 54 spirals to form a thread to mate with a corresponding thread on the adaptor 35 or the syringe 2.

In another embodiment, a plurality of ribs 54 extends straight longitudinally, axially, and more preferably parallel with respect to the syringe orientation axis. The ribs 54 are equally spaced around the periphery of the upper portion 50 of the mounting hole 46. The size of the mounting hole 46 and size of the ribs 54 can be selected so as to loosely retain or guide the syringe 2 or adaptor 35. Alternatively, the size of the mounting hole 46 and size of the ribs 54 are selected so as provide a frictional or press fit of a desired pull-off force between the holder 40 and the adaptor 35 or the syringe 2. In either case, conventional means for permanently attaching the adaptor 35 and/or syringe 2 to the holder 40, including but not limited to adhesives, solvent sealers, heat welding, or ultrasonic welding, can be used, if desired.

One skilled in the art will appreciate from this disclosure that other means for permanently or temporarily retaining the syringe 2 on the holder 40 are possible. An interlocking lug and slot system can be used on the holder 40 and the syringe 2 or adaptor 35. The body 42 can include a clip, clamp or other fastener (not shown) thereon to hold the syringe 2 in the desired orientation.

The mounting hole 46 is formed in a substantially cylindrical core portion 56 of the body 42. An elongated finger 58 extends outwardly from the core portion 56 of the body 42 and the syringe orientation axis 48. The finger 58 is connected, and more preferably rigidly attached, to the body 42.

The finger 58 extends in at least a radial direction with respect to the syringe orientation axis 48. The finger 58 also extends slightly upward in an axial direction with respect to the syringe orientation axis 48 in the embodiment shown.

Figure 4:
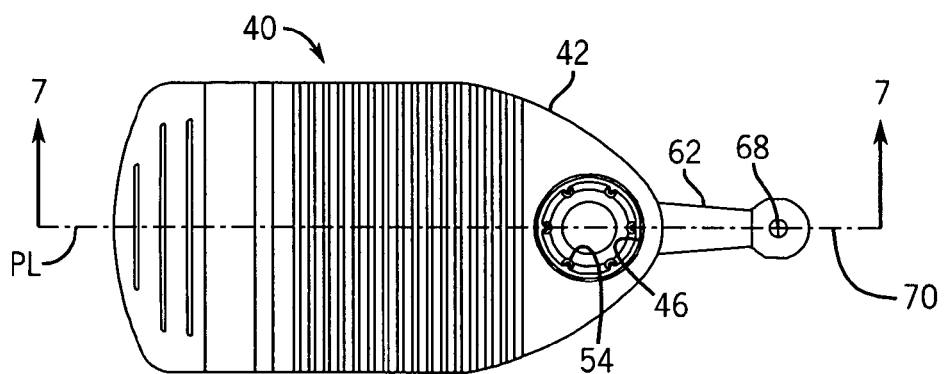
FIG. 4 is a top plan view of the syringe holder of FIG. 2.

The finger 58 has proximal end 60 that is connected to the core portion 56 of the body 42, an intermediate portion 62 and a distal end 64. The distal end 64 can be shaped in a variety of ways to allow sliding and pivotal movement of the syringe holder 40 in a plurality of planes. Although curved frusto-conical and barrel shapes would suffice, the distal end 64 more preferably has a ball 66 formed thereon. The ball 66 is preferably substantially spherical. Although other shapes, including but not limited to prismatic or cylindrical would suffice, the intermediate portion 62 is preferably conical and tapers uniformly from a first diameter adjacent to the proximal end 60 to a second diameter that is smaller than the first diameter and adjacent to the distal end 64 or ball 66. The diameter of the ball 66 is greater than the second diameter of the intermediate portion 62. The ball 66 has a center 68, which also resides on a central longitudinal axis 70 of the finger 58. As best seen in FIG. 4, the central longitudinal axis 70 resides in the same vertical plane as a parting line PL that bisects the body 42 and mounting hole 46. The parting line PL is at right angles with or perpendicular to the syringe orientation axis 48.

In addition to the core portion 56, the body 42 has a stop member 72 connected to the core portion 56. One skilled in the art will appreciate from this disclosure that the stop member 72 can extend from the core portion 56 in whatever direction is necessary to engage or abut the pump 6. In the embodiment shown, the stop member 72 extends outwardly in a transverse or generally radial direction from the core portion 56 and the syringe orientation axis 48. The stop portion 72 extends from the core portion 56 in a direction different than the finger 58, more preferably in a direction generally opposing the direction the finger 58 protrudes. In the embodiment illustrated, the stop member 72 extends or protrudes from the core portion 56 in an opposite direction than the finger 58. The mounting hole 46 is disposed or located between the finger 58 and the stop member 72.

The stop member 72 includes a beam 74, a clip 76, and an optional handle or lever 78. The clip 76 connects to the beam 74 and is adapted to detachably or releasably attach the syringe holder 40 to a portion of the pump 6, as will be described further below. The lever 78 connects to the beam 74 and allows the user to handle or apply pivotal force to the syringe holder 40.

The beam 74 has an upper portion that is an oblong plate 80 that extends generally horizontally. The top side or upper surface of the plate 80 may optionally include friction enhancing means, such as a groove or ridge, or more preferably a series of grooves or ridges 82 for example, to reduce the risk of slippage when the user pushes or pulls on the holder 40 via the plate 80. In the embodiment shown, equally spaced, parallel ridges 82 extend from adjacent the proximal end of the plate 80 where it is connected to the core portion 56 to the distal end of the plate 80. The ridges 82 extend transverse, or more preferably perpendicular, to the parting line PL.

The clip 76 connects to, or more preferably attaches to, the underside of the plate 80 adjacent to or near the distal end of the plate 80. The beam 74 can optionally include a neck 84 to further connect or attach the clip 76 to the core portion 56 of the body 42 and the plate 80 for greater support and stability. The neck 84 has a proximal end joined to the outer diameter of the core portion 56 and a distal end joined to the clip 76 and the plate 80. The clip 74 includes a first jaw 86 adjacent to the core portion 56 or the neck 84 (if present) and a second jaw 88 connected to the first jaw 86, preferably in a hinged manner. The connection can be direct or can take place indirectly through connection with the plate 80. More preferably, the second jaw 88 is rigidly attached to the first jaw 86 and the resiliency of the material provides the hinge or the desired releasable clamping action.

The free end of the second jaw 88 is generally S-shaped in a vertical cross-section, as best seen in FIG. 7. The free end of the second jaw 88 curves downwardly and inwardly at a gradually decreasing rate toward the first jaw 86, then it curves back away from the first jaw 86. This provides a narrow mouth 90 leading into a larger opening 92 between the jaws 86, 88. The opening 92 extends laterally across the body 42 and generally transverse to the direction that the finger 58 protrudes from the core portion 56 of the body 42. Although the location and direction of the opening 92 can be selected to meet the needs of the particular mounting arrangement or pump 6, the opening 92 in the illustrated embodiment extends perpendicular to the syringe orientation axis 48 and the mounting hole 46. The mounting hole 46 is located between the clip 76 or stop member 72 and the finger 58.

The optional handle or lever 78 has a generally L-shaped cross-section in a vertical plane, as best seen in FIG. 7. The lever 78 has a first leg 94 and a second leg 96 connected, or more preferably rigidly attached, to the first leg 94. In the embodiment shown, the second leg 96 is longer in the vertical cross-section than the first leg 94. As best seen in FIGS. 2-4 and 7, both legs 94, 96 are substantially planar plates similar to the plate 80. Similar to the upper surface of the plate 80, the second leg 96 has an upper surface that may optionally include friction enhancing means, such as a groove or ridge, or more preferably a series of grooves or ridges 98 for example, to reduce the risk of slippage when the user handles the lever 78. In the embodiment shown, a plurality of equally spaced, parallel ridges 98 extend from adjacent the proximal end of the second leg 96 where it is connected to the first leg 94. The ridges 98 extend transverse, or more preferably perpendicular, to the parting line PL and the forward projection of the finger 58. The ridges 98 extend parallel to the central axis of the opening 92.

The first leg 94 of the lever 78 can connect to the rest of the body 42 in various locations. The first leg 94 of the lever 78 can connect to the beam 74, at or near distal end of the plate 80. Alternatively, the first leg 94 can attach to the clip 76, which in turn is connected to the beam 74. The first leg 94 can attach to the outer surface of the second jaw 88 of the clip 76, opposite the opening 92. In the embodiment shown, the first leg 94 attaches to outer surface of the second jaw 88 at or near its junction with the first jaw 86 and the plate 80 of the beam 74.

The first leg 94 extends from the clip 76 or plate 80 at an angle α with respect to horizontal of approximately 45-180 degrees, more preferably approximately 90-165 degrees. In the embodiment shown, the angle α is approximately 135-150 degrees. The first and second legs 94, 96 can be joined together at various angles as well without departing from the present invention. The second leg 96 can extend from the first leg 94 at an included angle β of approximately 30-150 degrees, more preferably approximately 60-145 degrees, and even more preferably about 75-120 degrees. In the embodiment shown, the angle β is approximately 75-90 degrees. Attaching such a lever 78 near the opening 92 but generally opposite the mouth 90, provides an effective lever for pushing the clip 76 onto a structure on the pump 6 or for pulling on the clip 76 to release it.

In the embodiment shown, the syringe holder 40, including the core portion 56, finger 58, clip 76, stop member 72, is formed as a single, unitary, substantially rigid yet somewhat resilient member. Thus, the syringe holder 40 can be inexpensively made of a suitable commercially available plastic material using conventional molding techniques. Because the invention is used in a medical application, the material may need to be capable of withstanding heat or radiation sterilization cycles, as dictated by regulatory requirements in the United States and Europe. Thus, a radiation grade of acrylonitrile-butadiene-styrene (ABS) copolymer material is generally preferred.

FIGS. 8 and 9, show an infusion system 100 including a syringe holder 40 according to the present invention. The infusion system 100 includes a pump 6 and a syringe holder 40 for detachably mounting the syringe 2 on the pump 6 in a desired position and orientation. The syringe 2 can be detachably mounted on the holder 40 before or after the holder is installed on the pump 6. Although one skilled in the art will recognize that the invention is applicable to various types of medical pumps, including but not limited to enteral pumps, infusion pumps, syringe pumps and peristaltic pumps, the pump 6 in the embodiment shown is of the type that utilizes a cassette 16. Such a pump is referred to as a cassette pump. The pump 6 has a housing 7 and a handle 8 connected to the housing 7 for carrying the pump 6.

A locating socket 4 is provided on the pump 6 for the finger 58 of the syringe holder 40 to be longitudinally inserted into. Depending on the desired location and orientation of the syringe 2, the socket 4 can be provided in any convenient location. In the embodiment shown, the socket 4 is formed in the housing 7 at the backside of the display screen 9 of the pump 6. The socket 4 is generally opposite the carrying handle 8, which includes a rod or bar that extends in a generally horizontal direction across the back of the pump 6. The socket 4 can be formed solely for the syringe mounting function or advantageously can be defined by an existing screw hole on the housing 7. In the embodiment shown, the socket 4 extends substantially horizontally into the pump housing 7 so that the syringe holder 40 can orient the syringe 2 in a substantially upright position and the syringe orientation axis 48 is substantially upright, and more preferably vertical. The ball 66 on the distal end 64 of the finger 58 is sized to fit within the socket 4 and allow at least the distal end 64 of the finger 58 to be inserted longitudinally into the socket 4. The length of the finger 58 preferably is selected to exceed the depth of the socket 4.

The length of the beam 74 of the stop member 72 is selected so that it abuts a portion of the pump 6 that is remote from the socket 4, such as the handle 8 for example, once the finger 58 is inserted into the socket 4. More preferably the length of the beam 74 is selected so that the mouth 90 of the opening 92 between the jaws 86, 88 of the clip 76 is positioned over the handle 8. Once the finger 58 is inserted, the syringe holder 40 can still pivot in at least one plane. More preferably, the holder 40 can pivot in a plurality of planes (i.e., at least vertically and about the central longitudinal axis 70 of the finger 58). The walls of the socket 4 can be flared outwardly near the entrance of the socket 4 to provide clearance and further facilitate the insertion of the finger 58 of the syringe holder 40 and the pivoting of the syringe holder 40.

To mount the syringe holder 40 on the pump 6, the user grasps the holder 40 in a convenient location, including but not limited to the finger 58, the lever 78, the clip 76, the beam 74, or the plate 80. With the arrangement shown, the user positions the syringe holder 40 with the clip 76 facing down. Initially, the holder 40 should be held with the finger 58 tilted slightly downward and the other end of the holder 40 with the stop member 72 thereon should be elevated slightly so as to avoid the handle 8. The user longitudinally inserts the finger 58 into the socket 4 until the ball 66 on the distal end 64 of the finger 58 is in the socket 4 and the clip 76 is positioned over the pump handle 8. Then the user pivots the syringe holder 40 vertically by pushing the stop member 72 down to initially abut the pump handle 8 and limit pivot movement of the holder 40. To better secure the holder 40 against inadvertent movement with respect to the pump 6, the user then pushes down harder on the stop member 72 via the plate 80 or the lever 78. The jaws 86, 88 of the clip 76 resiliently flex apart so that the handle 8 can pass through the mouth 90, into the opening 92, and abut the underside of the plate 80. The mouth 90 has a narrowest width in a free or relaxed state that is initially smaller than the corresponding width of the handle 8 in a vertical plane. Therefore, as best seen in FIG. 9, the jaws 86, 88 resiliently clamp onto the handle 8 when the syringe holder 40 is fully snapped thereon. To release and remove the syringe holder 40, the user pulls up on the lever 78 with sufficient force to overcome the clamping force of the jaws 86, 88 and free the handle 8 from the opening 92 of the clip 76. The user pivots the stop member 72 above the handle 8 and then longitudinally withdraws the pivot finger 58 from the socket 4 to detach the syringe holder 40 from the pump 6.

The syringe holder 40 of the present invention provides great flexibility. The manufacturer or a user may detachably attach a syringe 2 to the holder 40 before or after the holder 40 is removably mounted on the pump 6. As previously described with reference to FIG. 1, the user or a manufacturer can detachably attach or mount a syringe 2 on the holder 40 when the holder is incorporated into a tube set assembly 10. With reference to FIGS. 10-13, a user can mount a conventional syringe 2 that is prefilled with a desired medicament on the syringe holder 40 in yet another way. The user removes the syringe 2 from its sealed package P and, keeping the end with the cap 102 thereon up, removes the cap 102 from the distal or discharge end 104 of the syringe 2. The discharge end 104 of the syringe 2 includes a conventional male luer fitment 106, an annular collar 108 around the fitment 106, and internal threads 110 on the annular collar 108, as disclosed in U.S. Pat. No. 5,807,345. The user turns the syringe holder 40 over so the plate 80 is facing down and inserts the discharge end 104 of the syringe 2 up into the mounting hole 46, which has an diameter adapted to guidingly receive, or more preferably retain with a slight manual press fit, the annular collar 108 of the syringe 2. The user then detachably secures the syringe 2 and the holder 40 to the tube 12 with an adaptor 35A. The adaptor 35A has a hole 36 therein for sealed fluidly coupling to the tube 12 as previously described, as well as a female luer cup 41 and at least one thread 43 for detachably connecting respectively to the male luer fitment 106 and internal threads 110 on the syringe 2. The user detachably attaches the syringe 2 to the adaptor 35A and the holder 40 by inserting adaptor 35A into the mounting hole 46 until the male luer fitment 106 extends into the female luer cup 41 on the adaptor 35A and the thread 43 engages the threads 110, then rotating the syringe 2, holder 40, or the adaptor 35A with respect to the syringe orientation axis 48.

From the foregoing, it can be seen that the present invention accomplishes at least all of the stated objectives.

While the invention has been described in connection with certain specific embodiments, it will be understood that many modifications, substitutions, and additions can be affected by one skilled in the art without departing from the intended broad scope of the invention defined in the claims that follow.

What is claimed is:

1. A syringe holder for detachably mounting a syringe on a medical pump, the syringe holder comprising:
   a body;
   a syringe retainer connected to the body, the syringe retainer comprising a hole configured to hold a syringe, the hole centered around a first axis;
   an elongated finger extending outwardly from the body, the elongated finger being adapted to be inserted into a socket on a medical pump so as to permit pivotal movement of the syringe holder in a plurality of planes once inserted, the elongated finger comprising a distal end that comprises a ball and a proximal end connected to and extending outwardly from and along a second axis; and
   a stop member connected to the body, the stop member comprising a clip configured to removably attach to the medical pump to limit the pivotal movement of the syringe holder, the clip comprising an opening centered around a third axis which extends transverse to the first axis.

2. A syringe holder in accordance with claim 1, wherein the clip comprises a first jaw connected to a second jaw.

3. The syringe holder in accordance with claim 2, wherein the first jaw comprises a portion of the body, and the second jaw is flexibly connected to the body.

4. The syringe holder in accordance with claim 3, further comprising a handle attached to and extending outwardly from the body, the handle aligned at least partially above the opening and configured to move the second jaw away from the first jaw.

5. A syringe holder in accordance with claim 1, wherein the hole is located between the elongated finger and the stop member.

6. A syringe holder in accordance with claim 1, wherein the hole extends through opposed outer surfaces of the body.

7. A syringe holder in accordance with claim 1, wherein the elongated finger comprises a continuously tapered intermediate portion extending outwardly along the second axis between the proximal end and the distal end, the continuously tapered intermediate portion being conical and having a first diameter adjacent the proximal end and a second diameter adjacent the distal end, wherein the second diameter is smaller than the first diameter.

8. A syringe holder in accordance with claim 1, wherein the body, the elongated finger, and the stop member comprise a single unitary piece of material.

9. A syringe holder in accordance with claim 1, wherein the stop member is disposed at one end of the body and the elongated finger is disposed at another end of the body.

10. The syringe holder in accordance with claim 1, wherein the opening is circular.

11. A tube set assembly for a medical pump, comprising:
    a tube;
    an adaptor fluidly coupled with the tube; and
    a syringe holder connectable to the tube and comprising:
      a body;
      a syringe retainer connected to the body, the syringe retainer comprising a hole configured to hold a syringe, the hole centered around a first axis;
      an elongated finger extending outwardly from the body, the elongated finger being adapted to be inserted into a socket on a medical pump so as to permit pivotal movement of the syringe holder in a plurality of planes once inserted, the elongated finger comprising a proximal end connected to and extending outwardly from and along a second axis, and a distal end that comprises a ball; and
      a stop member connected to the body, the stop member comprising a clip configured to removably attach to the medical pump to limit the pivotal movement of the syringe holder, the clip comprising an opening centered around a third axis which extends transverse to the first axis.

12. A tube set assembly according to claim 11, wherein the adaptor is mounted in the hole.

13. A tube set assembly according to claim 12, wherein the syringe is detachably mounted to the adaptor and extends along the first axis.

14. A tube set assembly according to claim 13, further comprising a cassette connected to the tube.

15. A tube set assembly according to claim 11, wherein the stop member is disposed at one end of the body and the elongated finger is disposed at another end of the body.

16. A tube set assembly according to claim 11, wherein the elongated finger comprises a continuously tapered intermediate portion extending outwardly along the second axis between the proximal end and the distal end, the continuously tapered intermediate portion being conical and having a first diameter adjacent the proximal end and a second diameter adjacent the distal end, wherein the second diameter is smaller than the first diameter.

17. The tube set assembly according to claim 11, wherein the clip comprises a first jaw connected to a second jaw, the first jaw comprising a portion of the body and the second jaw being flexibly connected to the body, and further comprising a handle attached to and extending outwardly from the body, the handle aligned at least partially above the opening and configured to move the second jaw away from the first jaw.

18. The tube set assembly according to claim 11, wherein the opening is circular.

19. An infusion system comprising:
a medical pump having a socket formed thereon; and
a syringe holder detachably mounted on the medical pump and comprising:
  a body;
  a syringe retainer connected to the body;
  an elongated finger extending outwardly from the body, the elongated finger inserted into the socket on the medical pump removably connecting the syringe holder to the medical pump; and
  a stop member connected to the body, the stop member being removably attached to the medical pump limiting pivotal movement of the syringe holder.

20. An infusion system according to claim 19, further comprising a syringe detachably attached to the syringe retainer.

21. An infusion system according to claim 20, wherein the syringe retainer comprises a hole in the body extending transversely to a longitudinal axis of the body, the syringe is attached within the hole, and the elongated finger extends outwardly from the body along the longitudinal axis.

22. The infusion system according to claim 21, wherein the hole extends through opposed outer surface of the body.

23. An infusion system according to claim 19, wherein the medical pump includes a handle and the stop member is a clip having jaws removably clamped onto the handle.

24. An infusion system according to claim 20, wherein the medical pump is a cassette pump and the syringe held by the syringe holder is fluidly connected to a tube set that includes a cassette.

25. The infusion system according to claim 23, wherein one of the jaws comprises a portion of the body and another of the jaws is flexibly connected to the body.

26. The infusion system according to claim 19, wherein when the stop member is detached from the medical pump the elongated finger pivots within the socket of the medical pump allowing the syringe holder to pivot relative to the medical pump.

27. The infusion system of claim 19, wherein the body, the elongated finger, and the stop member comprise a single unitary piece of material.

28. The infusion system of claim 19, wherein the syringe holder further comprises a handle attached to and extending outwardly from the body which is configured to detach the stop member from the medical pump and to reattach the stop member to the medical pump.

29. An infusion system according to claim 19, wherein the stop member is disposed at one end of the body and the elongated finger is disposed at another end of the body.

* * * * *